(12) United States Patent
Wang

(10) Patent No.: US 12,377,057 B2
(45) Date of Patent: *Aug. 5, 2025

(54) ARTERIAL APPLICATION OF LOW DOSE ETHYL ALCOHOL ENABLES BLOOD-BRAIN BARRIER (BBB) TRANSIENT OPENING

(71) Applicant: Weijun Wang, San Gabriel, CA (US)

(72) Inventor: Weijun Wang, San Gabriel, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/001,374

(22) Filed: Dec. 24, 2024

(65) Prior Publication Data
US 2025/0134830 A1    May 1, 2025

Related U.S. Application Data

(63) Continuation-in-part of application No. 17/689,969, filed on Mar. 8, 2022.

(60) Provisional application No. 63/159,078, filed on Mar. 10, 2021.

(51) Int. Cl.
| | | |
|---|---|---|
| *A61K 31/045* | (2006.01) | |
| *A61K 9/00* | (2006.01) | |
| *A61K 31/704* | (2006.01) | |
| *A61K 39/00* | (2006.01) | |
| *A61K 39/395* | (2006.01) | |
| *A61K 49/00* | (2006.01) | |
| *A61M 5/42* | (2006.01) | |

(52) U.S. Cl.
CPC .......... *A61K 31/045* (2013.01); *A61K 9/0019* (2013.01); *A61K 31/704* (2013.01); *A61K 39/3955* (2013.01); *A61K 49/006* (2013.01); *A61M 5/427* (2013.01); *A61K 2039/54* (2013.01); *A61M 2210/0693* (2013.01); *A61M 2210/125* (2013.01)

(58) Field of Classification Search
CPC .. A61K 31/045; A61K 9/0019; A61K 31/704; A61K 39/3955; A61K 49/006; A61M 5/427; A61M 2210/0693; A61M 2210/125
See application file for complete search history.

(56) References Cited

FOREIGN PATENT DOCUMENTS

WO    WO2019/157195 A1 *  8/2019  .......... A61K 31/045

OTHER PUBLICATIONS

Takeda, N., Diksic, M. Relationship Between Drug Delivery and the Intra-arterial Infusion Rate of SarCNU in C6 Rat Brain Tumor Model. J Neurooncol. (1999) 41, 235-246 (Year: 1999).
Haorah, J., Heilman, D., Knipe, B. et al. Ethanol-induced activation of myosin light chain kinase leads to dysfunction of tight junctions and blood-brain barrier compromise. Alcoholism, Clinical and Experimental Research (2009) 29, 999-1009. (Year: 2009).
William M. Pardridge, Blood-brain barrier delivery, Drug Discovery Today, vol. 12, Issues 1-2 (2007) 54-61 (Year: 2007).

* cited by examiner

*Primary Examiner* — Joseph K McKane
*Assistant Examiner* — David M Shim
(74) *Attorney, Agent, or Firm* — Novoclaims Patent Services LLC; Mei Lin Wong

(57) ABSTRACT

A method of inducing blood-brain barrier (BBB) opening for delivery of a non-BBB permeable substance to a subject includes the steps of: administering an ethyl alcohol at 0.01%-5% v/v into an arterial bloodstream via arterial injection guided by ultrasound and inducing a homogeneous distribution of the non-BBB permeable substance in a brain parenchyma. The ethyl alcohol reaches a brain of the subject to induce a transient opening of blood-brain barrier so that the non-BBB permeable substance can penetrate the blood-brain barrier to reach the brain and its concentration can be adjusted precisely by serial dilution. The non-BBB substance includes a therapeutic agent, a diagnostic agent, or a prophylactic agent. The use of low concentration of ethyl alcohol can induce a temporary BBB opening for about 120 minutes and then the BBB can be restored to normal without causing significant harmful effect.

15 Claims, 9 Drawing Sheets

ARTERIAL APPLICATION OF LOW DOSE ETHYL ALCOHOL ENABLES BLOOD-BRAIN BARRIER (BBB) TRANSIENT OPENING

CROSS REFERENCE OF RELATED APPLICATION

This is a Continuation-In-Part patent application of Ser. No. 17/689,969, filing date Mar. 8, 2022, which is a non-provisional patent application claiming the priority of U.S. provisional patent application No. 63/159,078, filed Mar. 10, 2021, which is incorporated herein by reference in their entirety.

BACKGROUND OF THE PRESENT INVENTION

Field of Invention

The present invention relates to opening the blood-brain barrier (BBB), and more particularly to an improved method of opening the BBB transiently with low-dose ethyl alcohol (EA) with increased safety, precision, control, and its applications.

Description of Related Arts

The blood-brain barrier (BBB) is a dynamic biological interface that controls the exchange of substances between the blood and the central nervous system (CNS). The structural and functional integrity of the BBB is vital for the maintenance of homeostasis in the CNS. However, from the treatment perspective, it impedes the entry of drugs into the CNS. It prevents many potent pharmaceutical agents from exerting substantial therapeutic activity against CNS disorders and brain-related malignancies.

Different strategies have been tried, such as intracranial (intracerebroventricular, intraparenchymal, and intrathecal) administration, intranasal delivery, the ultrasound-induced opening of the BBB, and even BBB disruption via rapid intracarotid infusion of a hyperosmolar mannitol solution. However, none of these can produce a satisfactory result.

Since the concept of osmotic BBB opening was introduced in 1972, the hyperosmotic mannitol has been used in the clinic for decades as a vehicle to transiently open BBB to deliver medications into the brain. Mannitol has a chemical formula $C_6H_{14}O_6$, a molecular mass of 182.172 g/mol, and a chemical structure as shown in FIG. 1A.

Intra-arterial (IA) infusion of hyperosmolar mannitol represents the main clinical method to open the BBB transiently. However, the fluctuations in BBB opening mediated by mannitol may have a severe negative impact on the regional delivery of therapeutics, along with unpredictable adverse effects, such as seizures, risks of brain embolism, catastrophic bleeds, and even fatal brain edema. There is an urgent medical need in the current medical practice to obtain a novel approach to transiently open the BBB in a safer and more controllable manner.

Another compound that is studied for transient BBB disruption is NEO100. NEO100 is a highly concentrated, cGMP-manufactured version of perillyl alcohol (POH). It is a naturally occurring monoterpene related to limonene that is present in the essential oils of citrus fruits and other botanicals, such as sage, peppermint, cherries, and celery seeds. The concept of intracardiac injection of NEO100 was introduced and used in the preclinical to transiently open BBB and deliver medications into the brain. NEO100 has a chemical formula $C_{10}H_{16}O$, a molecular mass of 152.23 g/mol, and a chemical structure as shown in FIG. 1B.

NEO100 demonstrated a great potential to open BBB when applied by intracardiac (IC) injection. The intracardiac NEO100-mediated BBB opening is in a dose-dependent manner. Due to its lipophilic property, the suspended NEO100 in water solution can cause a random, haphazard, unhomogenized BBB disruption and lead to a patchy, punctate, or uneven distribution of extravasated EB (Evans Blue) dye inside the brain tissues.

The characterized "random or haphazard" means the NEO100 lacks a definite target or aim. The induced BBB disruption by this nonhomogeneous solution truly depends on where these suspended lipophilic/oily 100% NEO100 particles are attached to and damage the corresponsive arterial vasculature vessel wall.

Due to the unstable and unhomogenized suspension in the water or aqueous solution, NEO100 may fuse and form particles in varied sizes. It's not difficult to imagine that a large one could lead to the BBB opening in a patchy pattern, and a small one could lead to a punctate pattern. Even worse, no appropriate solvent is yet to dissolve and dilute NEO100 to the desired lower concentrations.

Other than that, NEO100 fails to provide a controllable, reliable, and safe transport mechanism to deliver therapeutics to the brain for the future treatment of CNS disorders.

Patients with brain tumors or brain metastasis are treated with multi-disciplinary approaches. The non-BBB permeable characteristics make it incapable of reaching an equivalent therapeutic efficacy in brain metastases as achieved in systemic malignancies. This pattern of failure has mainly been attributed to the lack of penetration of therapeutics to the CNS.

There is an urgent medical need to improve the transportation of BBB-impermeable therapeutics into the central nervous system (CNS), which is generally impeded by the blood-brain barrier (BBB). Thus, it is challenging to deliver a therapeutic, diagnostic, or prophylactic agent into the brain of a subject, such as an antibody for the targeted therapy or antibody fragment or provide a pharmaceutical composition to the brain of a subject.

BBB is supposed to be an innate defense system that regulates molecule transport into and out of the CNS (Central Nervous System) and prevents blood cells, plasma components, and pathogens from entering the brain by creating a tightly regulated nervous unit (NVU) that includes endothelial cells, pericytes, and astrocyte, all of which work together to preserve the chemical components of the neural environment to keep the brain function normally. Any pathological changes may cause a breach of BBB, which is always an unfavorable process and leads to some adverse effects. Therefore, the interval of the breached BBB matters and dramatically impacts the safety of experimental animals and future human subjects. Nevertheless, under some circumstances, a safe and controllable transient BBB opening can produce profound impacts and dramatic clinical significance to achieve better therapeutic efficacy.

SUMMARY OF THE PRESENT INVENTION

An object of the present invention is to provide a method of inducing an immediate, efficient, transient, reversible, and safe BBB opening for facilitating a brain penetration of non-BBB permeable therapeutics of different sizes.

Another object of the present invention is to provide a method of inducing an immediate, efficient, safe, and controllable transient BBB opening to facilitate the brain distribution of non-BBB-permeable therapeutics. Thus, drug delivery to target brain malignancies and CNS disorders can be achieved in a controlled and safe manner to replace the random, haphazard, unhomogenized spread of those non-BBB permeable substances.

Another object of the present invention is to provide a method of opening BBB in a safe, homogenized, and controllable manner so that the transient BBB permeabilization effect can be achieved without causing devastating adverse effects.

Another object of the present invention is to provide an improved method of EA-mediated transient BBB opening in a much shorter reversible time to minimize the devastating adverse effects on the natural protection mechanism.

Another object of the present invention is to provide a method of delivery of a therapeutic, diagnostic, or prophylactic agent, such as those targeting brain malignancies and CNS disorders, into the brain tissues of a subject in a controllable manner.

Another object of the present invention is to provide a method of delivering an antibody or antibody fragment into the brain of a subject in a safer and more controllable manner compared to the random, haphazard, uneven spread of the non-BBB permeable substance inside the brain tissues, such as via the IA NEO100-mediated BBB disruption.

According to a preferred embodiment of the present invention, a method of inducing a transient blood-brain barrier (BBB) opening for delivery of a non-BBB permeable substance to a brain of a subject, comprises the steps of: preparing an ethyl alcohol having a predetermined concentration by serial dilution with purified water or 0.9% NaCl; administering the ethyl alcohol into an arterial bloodstream of the subject via intra-arterial (IA) injection, or ultrasound-guided intracardiac injection, wherein the ethyl alcohol (EA) has a concentration of 0.01%-5% v/v, preferably at 0.1%-0.3% v/v, at the injection site, and the ethyl alcohol (EA) reaches the brain of the subject to induce a transient opening of the blood-brain barrier for an opening time frame of not more than 2 hours (120 minutes) so that the non-BBB permeable substance is capable of penetrating the blood-brain barrier to reach the brain of the subject during the opening time frame. Then, the BBB is restored to normal status after the opening time frame without significant harmful effects, serving the normal function of blocking the non-BBB permeable substance from entering the brain. The non-BBB substance comprises a therapeutic agent, a diagnostic agent, or a prophylactic agent, and is administered to the subject before, at the same time with, or within 120 minutes after the ethyl alcohol (EA) is administered to the subject.

Intraarterial ethyl alcohol (EA) can reduce the level of tight junction proteins for about 120 minutes immediately after being administered to the subject. The concentration of the EA can be adjusted using USP water or 0.9% NaCl. When EA is administered through a left-side intraarterial catheter placement, the non-BBB substance can be localized mainly to the left side of the brain.

When the EA is administered via ultrasound-guided intracardiac injection, an infusion flow rate of intra-arterial injection or intracardiac injection is about 5-7 µl/second (0.3-0.45 ml/min), and an infusion volume is about 10% of the body weight (at 1 µl/g, volume/weight ratio) of the subject.

The non-BBB permeable substance is selected from one or more of the following: a small molecular tracer, Evans blue dye, a cancer therapeutic agent, doxorubicin, an antibody, an antibody fragment, Trastuzumab, a checkpoint inhibitor, an anti-PD1 antibody or a PD1-binding fragment thereof, a monoclonal antibody, a peptide, a growth factor, a cytokine, and an enzyme.

According to another aspect of the present invention, a preferred embodiment of the present invention provides a method for the delivery of a therapeutic agent, a diagnostic agent, or a prophylactic agent into the brain of a subject, which comprises the following steps:

adjusting a predetermined concentration of ethyl alcohol by using purified water or 0.9% NaCl; administering the ethyl alcohol into an arterial bloodstream of the subject, wherein a preferable concentration of the ethyl alcohol is 0.1%-0.3% v/v; and administering an effective amount of the therapeutic agent, the diagnostic agent, or the prophylactic agent before, concurrently or not more than 120 minutes after the ethyl alcohol is administered, wherein said ethyl alcohol reaches a brain of the subject to induce a transient opening of blood-brain barrier so that the of the therapeutic agent, the diagnostic agent, or the prophylactic agent penetrates the blood-brain barrier to reach the brain of the subject. Then, the blood-brain barrier is restored to normal after 120 minutes without causing significant harmful effects to the brain, serving its normal function to block the non-BBB permeable substance from entering the brain Intraarterial ethyl alcohol (IA EA) reduces the tight junction proteins in the BBB for no longer than 120 minutes immediately after EA is administered to the subject. The concentration of EA is adjusted by serial dilution using purified water or sodium chloride, both of which meet the USP standard.

Preferably, the ethyl alcohol (EA) is administered via intra-arterial or, ultrasound-guided intracardiac injection, an infusion flow rate of intra-arterial injection or intracardiac injection is about 5-7 µl/second (0.3-0.45 ml/min). An infusion volume is about 10% of the subject's body weight (at 1 µl/g, volume/weight ratio).

The therapeutic agent, the diagnostic agent, or the prophylactic agent is one or more of: a small molecular tracer, EB dye, a cancer therapeutic agent, doxorubicin, an antibody, an antibody fragment, Trastuzumab, a checkpoint inhibitor, an anti-PD1 antibody or a PD1-binding fragment thereof, a monoclonal antibody, a peptide, a growth factor, a cytokine, and an enzyme.

Compared to Mannitol and NEO100, the use of IA ethyl alcohol-mediated BBB opening according to the present invention has the following advantageous effect:

Ethyl alcohol (EA) is a small molecule and water-soluble, with a molecular weight of 46.068 g/mol, as shown in FIG. 1C.

Ethyl alcohol can be easily produced under CMC (chemical manufacturer control).

Human beings have long used ethyl alcohol (EA) and consumed it for centuries in every corner of the world. Thus, the GMP grade and USP grade of ethyl alcohol can be easily produced. In other words, the composition of ethyl alcohol has a higher safety level.

The pros and cons of EA are well-known. Unfortunately, ethyl alcohol has not been applied as a therapeutic agent in the current medical practice yet to disrupt the integrity of BBB and deliver life-saving medications for some dismal and poor prognosis diseases that are commonly seen in the clinic, such as the most malignant primary glioblastoma multiforme (GBM), the secondary breast cancer brain metastasis, and some refractory neurodegenerative diseases, including Alzheimer's Disease (AD), and Parkinson's disease (PD), etc.

In recent years, the American Food and Drug Administration (FDA) has approved several new drugs, including the antibodies Trastuzumab and T-DM1 (Kadcyla, ado-trastuzumab emtansine) for treating breast cancer and breast cancer brain metastasis, as well as aducanumab and lecanemab for the management of Alzheimer's disease (AD).

Due to the BBB's bottlenecks or roadblocks, delivering these large molecular antibodies into the brain would be crucial and challenging to achieve their potent pharmacological efficacy. Addressing this problem would represent a revolutionary change in drug delivery methods in current medical practice and improve the therapeutic efficacy of these CNS-related disorders.

Because of its infinitely soluble (fully miscible) in water, ethyl alcohol (EA) can be easily diluted into any lower concentration desired by serial dilution and is evenly distributed in the solution. Also, due to the uniformity of the solution, ethyl alcohol demonstrated a more predictable and reliable result in inducing BBB opening. No uneven unpredictable patchy spots has resulted.

To limit the extent of opened BBB, ethyl alcohol (EA) can be manipulated via an intraarterial catheter to lead to a localized BBB (a segment of a cerebral artery) opening.

IA EA can cause an even, homogeneous BBB opening, which is much safer than the NEO100-induced opening, which has caused a random, haphazard, uncontrollable, patchy, or punctate pattern, preventing some devastating adverse effects and even life-threatening situations.

IA EA can decrease the requirements of certain variables of BBB opening compared to IA mannitol due to multiple factors that may interfere with its efficacy. The variables include the volume applied, the speed of injection, the temperature of mannitol applied, etc.

BRIEF DESCRIPTION OF THE DRAWINGS

FIG. 2 illustrates the photographs of the perfused brain tissues from experimental mice treated with various concentrations of ethyl alcohol (EA), mannitol, and NEO100 concurrent with Evans Blue (EB) dye.

FIGS. 10A & 10B illustrate the significant difference between IA EA and IA NEO100-mediated BBB opening in the experimental mice in Comparative Experiment 19.

DETAILED DESCRIPTION OF THE PREFERRED EMBODIMENT

According to the preferred embodiment of the present invention, a method of inducing an immediate, efficient, reversible, controllable, safe, and transient blood-brain barrier (BBB) opening for facilitating a brain distribution of non-BBB permeable therapeutics of different sizes comprises the steps of:

administering a composition comprising an effective amount of ethyl alcohol (EA) as the sole BBB opening vector into the arterial bloodstream via ultrasound-guided intracardiac (IC) injection or intraarterial injection.

Figure 1A:
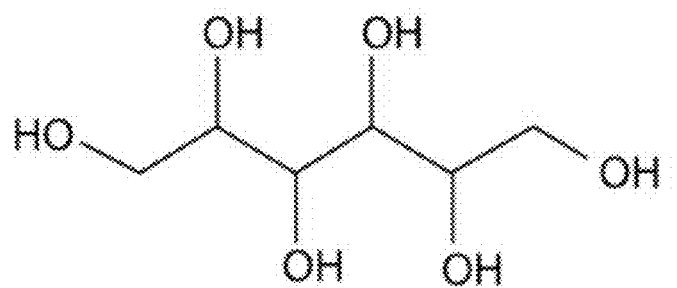
FIG. 1A illustrates the chemical structure of mannitol.
Figure 1B:
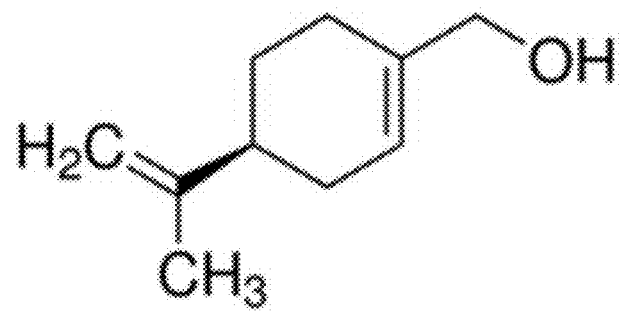
FIG. 1B illustrates the chemical structure of NEO100.
Figure 1C:
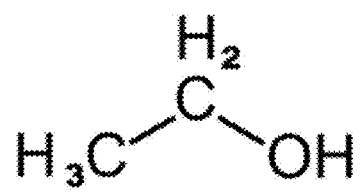
FIG. 1C illustrates the chemical structure of ethyl alcohol (EA) according to the present invention.

The ethyl alcohol (EA) has a chemical formula $C_2H_5OH$ and a chemical structure as shown in FIG. 1C of the drawings.

The molar mass of ethyl alcohol is 46.068 g/mol.

Ethyl alcohol (EA) can mediate an immediate and efficient BBB opening when it is applied arterially for up to about 120 minutes without causing significant harmful adverse effects. The disrupted BBB allows for non-BBB permeable substances extravasated from the circulation into the brain parenchyma, ranging from small molecular tracer, such as EB, cancer therapeutic agent, and Doxorubicin, to large molecule antibodies, such as Trastuzumab, which has been broadly applied for the treatment of HER2 overexpressing breast cancer brain metastasis; and the checkpoint inhibitor, anti-PD1 (Programed Death) antibody brain entry as well.

The working concentration range of EA, which can be applied arterially, is 0.015-5.0% (v/v, in USP bacteriostatic sterile water, ID, DRR784, USP, Hospira, Inc., Lake Forest, IL, USA). Only if diluted and lowered to a specific low concentration does EA act as a vector to induce BBB opening for non-BBB-permeable therapeutic brain entry.

Due to polarity properties, the ethyl alcohol (EA) can be diluted using USP sterile water or 0.9% sodium chloride for injection. (USP standards are quality standards established by the United States Pharmacopeia.)

Due to the characteristics of small molecules and its infinitely soluble (fully miscible) in water, EA can be prepared into any desired working concentration. Also, EA per se is a super powerful agent to disrupt the BBB even at a very low concentration, i.e., at 0.01%. On the other hand, EA has been living with human beings for years, decades, and even centuries due to its beneficial effects. In other words, EA is safe for use.

Compared to mannitol and NEO100, EA induces an immediate, efficient, reversible, transient, and safe BBB opening in experimental mice without causing significant harmful effects. Arterial EA-mediated BBB permeabilization facilitates the brain distribution of non-BBB permeable therapeutics of different sizes, including the extravasation of EB dye, and large molecule antibody, Trastuzumab. EA has a positive revolutionary impact on drug delivery of therapeutics to target brain malignancies and CNS disorders, providing an even distribution of non-BBB substance delivery to the brain with high precision and safety during a short time frame while allowing the BBB to restore to its normal function without causing significant harmful effect.

According to another preferred embodiment of the present invention, a method for delivery of a therapeutic, diagnostic, or prophylactic agent into the brain of a subject, comprising the steps of:
  administering a composition comprising an effective amount of EA into the arterial bloodstream, wherein the therapeutic, diagnostic, or prophylactic agent is extravasated from the bloodstream into the subject's brain or central nervous system (CNS).

Preferably, the method further comprises administering the therapeutic, diagnostic, or prophylactic agent into the arterial bloodstream of the subject.

Preferably, the therapeutic, diagnostic, or prophylactic agent is administered before or concurrently with the composition comprising the ethyl alcohol. The therapeutic, diagnostic, or prophylactic agent can be administered within 15 minutes, 60 minutes, but no longer than 120 minutes following the administration of the composition comprising the ethyl alcohol. The transient BBB opening, which has an opening window of about 120 minutes. Then, a complete recovery is followed to maintain its protective function and block the non-BBB permeable substance from brain entry.

The composition comprises ethyl alcohol (EA) at 0.015%-5% v/v. Preferably, the composition comprises ethyl alcohol at 0.01%-0.1% v/v, 0.1%-0.5% v/v, 0.5%-1% v/v, 1%-2% v/v, 2%-3% v/v, 3%-4% v/v, or 4%-5% v/v.

The composition comprises EA and a pharmaceutically acceptable carrier, wherein the pharmaceutically acceptable carrier includes USP bacteriostatic water or an aqueous solution containing USP sodium chloride (0.9% NaCl).

The composition is administered intra-arterially or via ultrasound-guided intracardiac injection via the puncture through the left ventricle.

Alternately, the composition comprising the ethyl alcohol (EA) is administered to a segment of a cerebral artery, thereby delivering the therapeutic, diagnostic, or prophylactic agent into a portion of the brain around the artery supplies.

The therapeutic, diagnostic, or prophylactic agent is impermeable or does not extravasate across a blood-brain barrier in a control subject that has not been administered with a composition comprising EA.

The therapeutic, diagnostic, or prophylactic agent comprises a small molecular tracer, Evans blue dye, a cancer therapeutic agent, doxorubicin, an antibody, an antibody fragment, Trastuzumab, a checkpoint inhibitor, an anti-PD1 antibody or a PD1-binding fragment thereof, a monoclonal antibody, a peptide, a growth factor, a cytokine, an enzyme, or a combination thereof.

The composition does not include mannitol, perillyl alcohol (NEO100), or both.

The subject is diagnosed with or suffers from, a brain tumor, brain metastasis, brain malignancy, or a CNS disorder.

According to another preferred embodiment of the present invention, a method for delivering an antibody or antibody fragment into the brain of a subject comprises administering a composition comprising an effective amount of ethyl alcohol and an effective amount of the antibody or antibody fragment in the subject's bloodstream, wherein the antibody or antibody fragment is extravasated from the bloodstream into the brain or central nervous system (CNS) of the subject.

The subject is a mammalian subject having a brain tumor, brain metastases, brain malignancy, or a CNS disorder, optionally a glioma, and the antibody or antibody fragment comprises Trastuzumab or an anti-PD-1 antibody or a combination thereof.

The subject has been administered with the composition within 2 hours (120 minutes) or less has a reduced level of an occludin, a claudin, and/or a Junction adhesion molecule in at least a portion of the blood-brain barrier, compared to a control subject.

According to another preferred embodiment of the present invention, the present invention provides a pharmaceutical composition comprising EA at 0.3% (v/v) and a pharmaceutically acceptable carrier. The pharmaceutically acceptable carrier includes water or sodium chloride with USP standard.

Material and Methods for Experiments

According to the preferred embodiment of the present invention, intraarterial (IA) or ultrasound-guided intracardiac injection (IC) is employed. The method of IA and IC injection is similar to the IV push in the clinic, which comprises essentially the steps of:
  pushing the injection composition at a particular infusion flow rate immediately after the placement of the IA catheter into the internal carotid artery (ICA) or the insertion of the injection needle into the left ventricle via the ultrasound-guided intracardiac (IC) puncture at room temperature.

When performing the IA and IC injections, the infusion flow rate is about 5-7 µl/second (0.3-0.45 ml/min), the infusion volume is about 10% of the body weight (at 1 µl/g, volume/weight ratio), and USP purified water or sodium chloride is used to reconstitute varied EA solutions at room temperature.

The various experimental infusion solutions which are used in the following experiments at least include the following:
1. 2% (w/v) Evans blue (EB) dye in H2O
2. 3% ethyl alcohol (EA) and 2% EB
3. IA 50 µg Goat anti-rat IgG (H+L)—ALEXA FLUOR® 647
4. IV 50 µg Goat anti-rat IgG (H+L)—ALEXA FLUOR® 647
5. 3% ethyl alcohol and IA 50 µg Goat anti-rat IgG (H+L)—ALEXA FLUOR® 647 (ab150167)
6. IA 10 µg Rabbit anti-human IgG (H+L)—ALEXA FLUOR® 647 (ab201841)
7. IV 10 µg Rabbit anti-human IgG (H+L)—ALEXA FLUOR® 647
8. IA 3% EA and 10 µg Rabbit anti-human IgG (H+L)—ALEXA FLUOR® 647 (ab201841)
9. IA 25% mannitol at 0.06 ml/second for 30 seconds As high-volume mannitol is required for IA injection to open BBB, therefore IV injection of 300 µl 2% EB via the tail vein will be done right after the IA mannitol application.

2 hours after the procedures, the experimental rats will be euthanized and perfused with 30 ml cold PBS (Phosphate-buffered saline).

In the following experiments, the sources of applicable EA used are as follows:
- 100% Pure 200 proof Culinary Solvent can be purchased from "The Northern Maine Distilling Company" 55 Baker Blvd, Brewer, Maine 04412.
- The alcohol made from Chinese liquor factory.
- 99.5% 200 proof pure ethyl alcohol can be purchased from Sigma Aldrich (Burlington, MA USA), Cat. #459836-100 ml.
- Dehydrated Alcohol, 200 Proof, Undenatured, USP from Spectrum Chemicals (Gardena, CA USA), Cat #ET107-100 ml.

Experiments for the ethyl alcohol mediated BBB disruption are performed and the injection method includes:
I. Intracardiac injection via left ventricle
II. Catheter placement via internal carotid artery
III. Intra-arterial (IA) Injection of ethyl alcohol accomplished by ultrasound-guided intracardiac (IC) puncture through the left ventricle:
IV. Ultrasound-guided IC injection of EA or NEO100 via the puncture of the left ventricle of the heart.

Intracardiac injection of NEO100 or EA can be carried out through the procedure of ultrasound-guided intracardiac (IC) injection. For example, ethyl alcohol is injected into the left ventricle (LV) of a mouse via ultrasound guidance. The mouse is anesthetized in an induction chamber using 2-3% isoflurane in 100% oxygen at a rate of 0.2-0.5 L/min. Fur over the thorax area is removed and the animal is placed in a stereotactic frame in supine position, securing the upper and lower limbs to avoid body movement. The ultrasound transducer is placed above the chest of the animal, and the injection syringe is anchored to a platform to avoid erratic needle movements. An electrocardiogram monitor is used to monitor heart function during the intracardiac injection. Injection of ethyl alcohol (0.3% in USP water or 0.9% sodium chloride, USP) is performed through a 30 G needle, and a total volume of 40 μL is injected over the course of 5 seconds.

The ultrasound-guided intracardiac (IC) injection is applied to replace the intraarterial (IA) ethyl alcohol injection. Different steps of the ultrasound-guided intracardiac puncture procedure include (a) carrying out 30 G needle puncture under the ultrasound; (b) carrying out percutaneous puncture of 30 G needle into the LV; (c) carrying out injection through the LV; and (d) observing normal heartbeat of the LV after the retraction of the injection needle.

The results of the above experiments showed that IA EA has a superior effect on transient BBB disruption when compared to IA NEO100. This includes the induced different BBB disruption pattern and a short interval window of the opened BBB, which leads to an even homogeneous spread of non-BBB permeable substances inside the brain tissues. More importantly, IA EA allows healthy recovery and restoration without causing substantial harmful effects. In other words, IA EA has a significant effect on transient BBB disruption while allowing healthy recovery and restoration without causing significant harmful effects.

Experiment 1: IA EA Mediated BBB Disruption for Delivering Extravasated EB Dye into the Brain IA ethyl alcohol at a selected range of 0.1%, 0.3%, 3%, and 5% are used on mice to test the effect of IA ethyl alcohol-mediated BBB disruption. EB dye is used as the non-BBB permeable substance. Any blue color observed in the brain indicates that the BBB is disrupted, and the extravasated EB dye is delivered to the brain. Photographs of the perfused brain tissues from the mice treated with IA NEO100, ethyl alcohol, and mannitol are taken for observation and comparison.

Results

Figure 2:
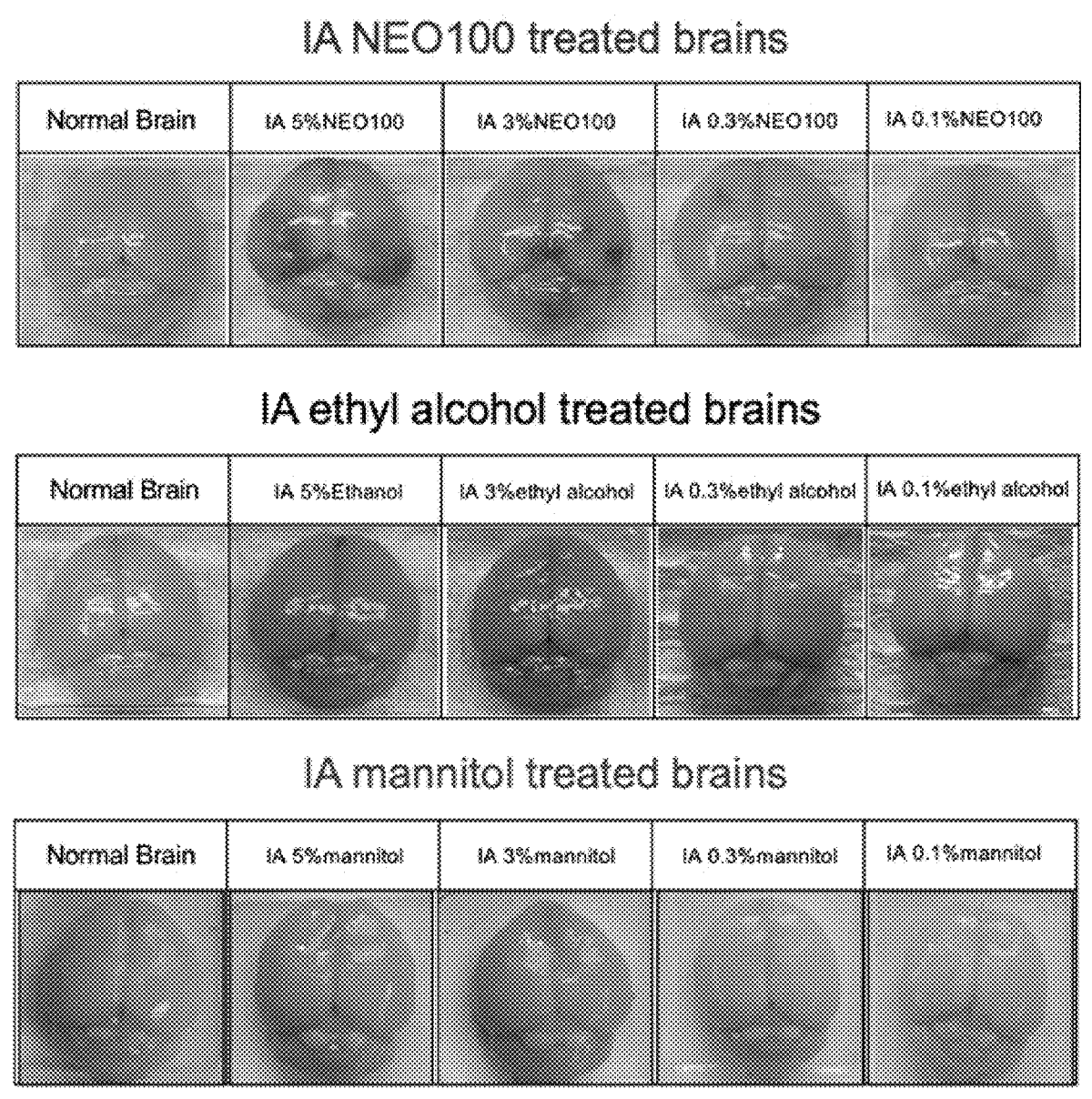

The photographs of the perfused brain tissues from the experimental mice treated with IA ethyl alcohol are shown in FIG. 2 of the drawings.

The perfused brain tissues of mice look blue when IA ethyl alcohol is used at 0.1%, 0.3%, 3%, and 5%. The blue is present in all parts of the brain, and no patchy pattern of blue color is observed.

The results of the efficacy of IA ethyl alcohol-induced BBB opening at a concentration of 0.1%, 0.3%, 3%, and 5% are summarized in Table 1 as follows:

TABLE 1

|  | 5% | 3% | 0.3% | 0.1% | Control |
|---|---|---|---|---|---|
| EB dye | Observed | Observed | Observed | Observed | Not Observed |
| EB dye penetration level | Widely spread in different parts of the brain | Widely spread in different parts of the brain | Widely spread in different parts of the brain | Widely spread in different parts of the brain | Not observed |
| Patchy Pattern of EB dye | Not observed | Not observed | Not observed | Not observed | Not observed |

The results showed that IA ethyl alcohol at 0.1%, 0.3%, 3%, and 5% could cause homogeneous BBB disruption and achieve a non-patchy or punctate distribution pattern of the non-BBB substance. In other words, IA ethyl alcohol effectively opens the BBB, leading to an even and homogeneous spread of non-BBB substances inside the brain tissues.

The potency of ethyl alcohol-induced BBB permeabilization and homogenized extravasation of EB dye are observed. The results show that ethyl alcohol can induce an immediate, transient, and recoverable BBB opening to deliver the non-BBB permeable substance.

Experiment 2: The Comparison of Extravasated EB Dye into Brain Parenchyma after IA ethyl alcohol, mannitol, and NEO100

The same procedure as Experiment 1 above is repeated, substituting ethyl alcohol with mannitol and NEO100. Photographs of the perfused brain tissues of the experimental mice after treatment are taken.

Results

These are photographs of the perfused brain tissues from the mice treated with IA mannitol and IA NEO100 at various concentrations. The images show the efficacy and major differences in the disruption of the BBB caused by the application of EA, NEO100, and mannitol.
1. The blue color can be observed in the brain of mice by using IA NEO100 at 0.1%, 0.3%, 3%, and 5%. The blue color is observed in all different parts of the brain. A patchy or punctate pattern of blue is observed. An overall blue color spreading over the entire brain is observed at 0.3%, 3%, and 5%. A few patchy spots are observed at 0.1%.

The results of the efficacy of IA NEO100-induced BBB opening at a concentration of 0.1%, 0.3%, 3%, and 5% are summarized in Table 2 as follows:

TABLE 2

|  | 5% | 3% | 0.3% | 0.1% | Control |
|---|---|---|---|---|---|
| EB dye | Observed | Observed | Observed | Observed | Not Observed |
| EB dye penetration level | Widely spread in different parts of the brain | Widely spread in different parts of the brain | Widely spread in different parts of the brain | Few Patchy spots | Not observed |
| Patchy Pattern of EB dye | Observed | Observed | Observed | Observed | Not observed |

Due to its lipophilic and water-insoluble properties, NEO100 induces a random, haphazard, uncontrollable, and unhomogenized disruption of the BBB. Furthermore, IA NEO100 leads to the spread of the non-BBB permeable substance, EB dye in a pattern of patchy or punctate extravasation in the perfused brain tissues.

When comparing the IA NEO100 and IA EA groups, the experimental mice treated with IA ethyl alcohol shows a more homogenized and evenly distributed pattern of EB dye spreading inside the perfused brain tissues.

2. The blue color cannot be observed in the perfused brain tissues from the mice treated with IA mannitol at 0.1%, 0.3%, 3%, and 5%. Some brain damage is observed.

The results of the efficacy of IA mannitol-induced BBB opening at a concentration of 0.1%, 0.3%, 3%, and 5% are summarized in Table 3 as follows:

TABLE 3

|  | 5% | 3% | 0.3% | 0.1% | Control |
|---|---|---|---|---|---|
| EB dye | Not observed | Not observed | Not observed | Not observed | Not observed |
| EB dye penetration | Not observed | Not observed | Not observed | Not observed | Not observed |

Mannitol is a hyperosmotic agent, which can cause the shrinkage of endothelial cells and physically tears the cell apart to permeabilize the BBB. Without the required procedure requirements, such as the volume applied, the speed of injection, and the temperature of mannitol applied, mannitol fails to cause BBB disruption. No disrupted BBB is observed from the mice when treated with IC application of varied volumes of high concentrations of mannitol.

The application of mannitol does not illustrate any effect of disrupting BBB under conditions similar to IA NEO100 and IA ethyl alcohol.

Experiment 3: Efficacy and Pattern of IA EA-Mediated BBB Disruption in Delivering EB Dye into the Brain IA ethyl alcohol at a selected range of 0.3%, 1%, and 3% are used on mice to test the effect of IA ethyl alcohol-mediated BBB disruption for delivering extravasated EB dye into the brain. Extravasated EB dye is used as the non-BBB permeable substance. Any blue color observed in the brain indicates that the BBB is disrupted, and the EB dye is delivered to the brain. Photographs of the perfused brain tissues at superior and sagittal views after IA ethyl alcohol treatment are taken for observation and comparison.

Results

Figure 3:
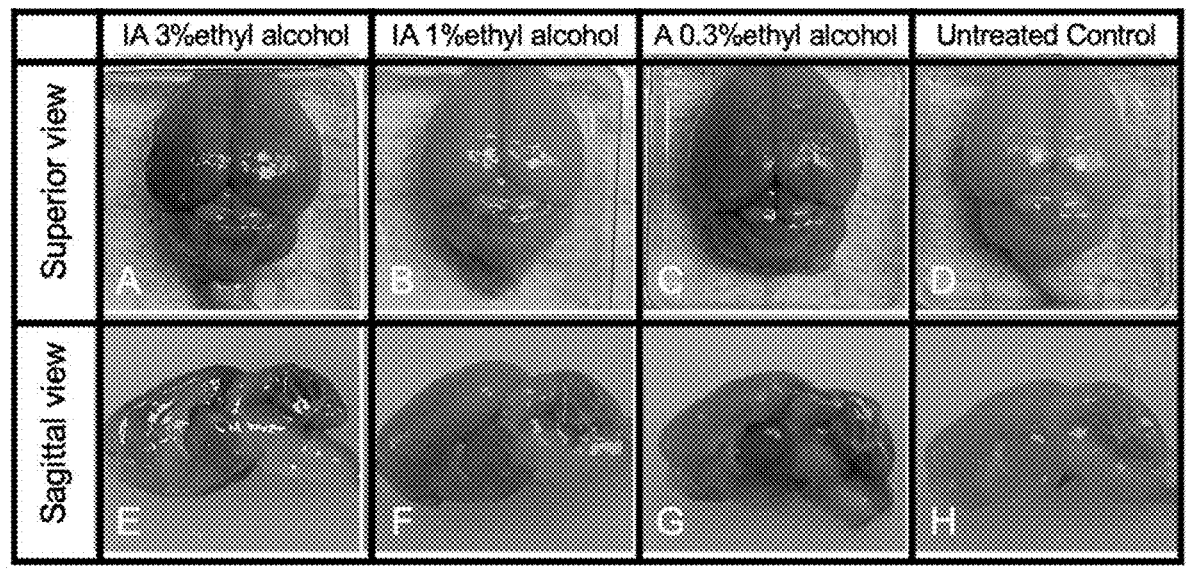
FIG. 3 illustrates the photographs of the perfused brain tissues from experimental mice treated with various concentrations of ethyl alcohol concurrent with 2% EB dye.

The photographs of the perfused brain tissues in superior and sagittal views from the experimental mice treated with IA ethyl alcohol at various concentrations are shown in FIG. 3 of the drawings.

The homogenized, evenly spread EB dye inside the brain tissues is observed when IA EA is at 0.3%, 1%, and 3%.

The results show that the IA ethyl alcohol-induced BBB opening is homogenized. Because ethyl alcohol is infinitely soluble (fully miscible) in water, it can be easily diluted into any lower concentration as desired. This homogenized pattern of BBB opening has important clinical significance. It indicates that the non-BBB substance can be delivered to the targeted brain tissue supplied by a special cerebral artery; therefore, the non-BBB substance is delivered in a controllable manner.

Experiment 4: Pharmacodynamic Study of IA EA-Induced BBB Opening

Four experimental groups were employed and treated with IA ethyl alcohol, and one untreated control group was without IA ethyl alcohol treatment. EB dye is used as the non-BBB permeable substance. For the four test groups, intra-arterial ethyl alcohol at 0.3% is administered to the animal subject. Then Evans blue is administered to the animal subject of four different groups following the ethyl alcohol administration at 15 min, 60 min, 120 min, and 240 min, respectively. Photos of the perfused brain tissues are taken for observations and comparisons.

Results

Figure 4:
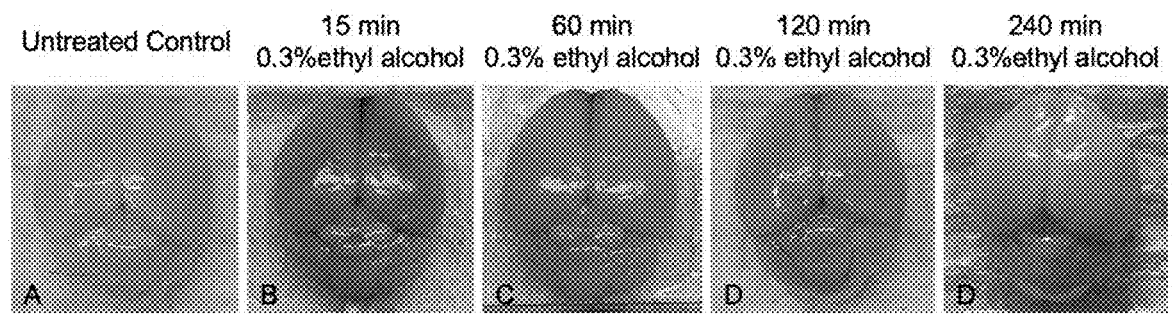
FIG. 4 illustrates the photographs of the perfused brain tissues from experimental mice treated with IA 0.3% ethyl alcohol followed by intravenous infusion of 2% EB dye at different timelines via tail vein catheter.

The photographs of the perfused brain tissues from the experimental mice treated with IA ethyl alcohol at 0.3% are shown in FIG. 4 of the drawings. The results demonstrated that lower doses (0.3%) of ethyl alcohol have great potential to induce a transient BBB disruption. As the lagged time of EB administration following EA administration increased, the level of blue color observed in the brain decreased. This shows that ethyl alcohol has a transient effect on BBB disruption.

Experiment 5: The Ultrastructure Changes after Applying IA Ethyl Alcohol Illustrated by TEM (Transmission Electronic Microscopy)

Figure 5:
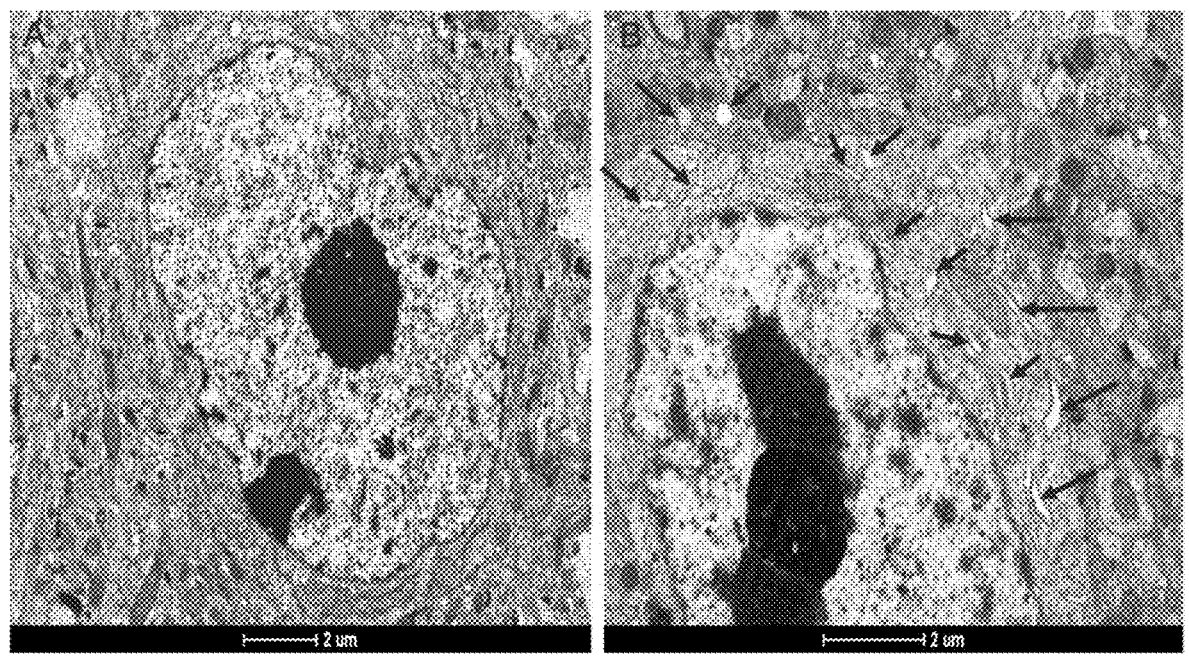
FIG. 5 illustrates the ultra-structure changes in the brain tissues acquired from the normal untreated experimental mouse and the mouse treated with IA 0.3% ethyl alcohol evaluated by Transmission Electronic Microscopy (TEM). The scale bar is 2 μm.

Ultrathin sections of the brains previously processed with Pelco BioWave Pro (Pelco, Fresno, CA USA) are cut at 99 nm and collected on 200-mesh copper grids. The grids are post-stained in uranyl acetate (0.2%) and filtered for 15 min. Grids are further stained with lead citrate and filtered for 5 min. The Tecnai Spirit G2TEM (Nanoscience Initiative, Nicholas Terrace, New York, USA) with an installed Mega View camera is used to image the samples. The micrographs are illustrated in FIG. 5 of the drawings. The scale bar is 2 µm.

The microstructure changes in brains from the animals treated with ethyl alcohol compared to normal untreated brain tissues by TEM (Transmission Electronic Microscope). As shown in FIG. 5, the micrograph A illustrates the ultrastructure of normal brain tissues without IA intervention of ethyl alcohol, and the micrograph B illustrates the ultrastructure of brain tissues with IA intervention of 0.3% ethyl alcohol. The ultrastructure of brain tissues with IA intervention of ethyl alcohol demonstrates many open spaces (pointed by blue arrowheads).

Experiment 6: Confocal Imaging of Trastuzumab with or without IA EA

Figure 6:
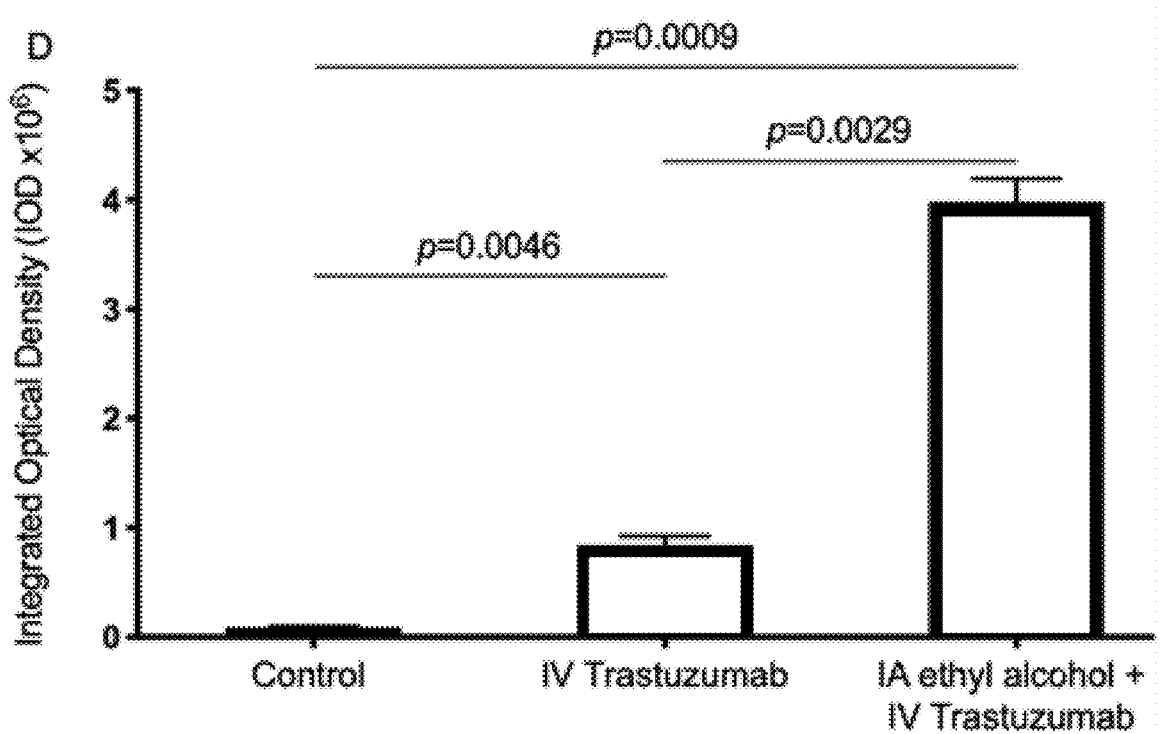
FIG. 6 illustrates the quantified antibody, Trastuzumab's accumulation inside the brain tumor tissues using confocal imaging when experimental mice bearing intracranial HER2-positive 4T1 breast cancer are treated with conventional IV Trastuzumab compared to IA ethyl alcohol+IV Trastuzumab.

The images acquired from the following three experimental groups: untreated control, IV Trastuzumab, and IA ethyl alcohol with IV Trastuzumab, are taken and analyzed. The analysis of the integrated optical density of the three animal groups is shown in FIG. 6 of the drawings. The image results demonstrate that IA ethyl alcohol can significantly enhance the antibody, Trastuzumab brain tumor entry, and accumulate exclusively inside the tumor.

Experiment 7

Confocal imaging to detect the extravasated antibody into the brain of the experimental mice, the checkpoint inhibitor, anti-PD-1 antibody-mediated by IA ethyl alcohol.

The standard detailed protocol is followed. Primary antibodies used are FITC-conjugated Armenian hamster anti-mouse PD-1 (11-9985-82, ThermoFisher Scientific, San Diego, CA USA), and rat anti-mouse PD-1 (BE0146, Bio X Cell, West Lebanon, NH USA). The secondary antibody is ALEXA FLUOR® 647 goat anti-rabbit (ab150083, Abcam). The images under different schedules of applications: Untreated control, IA Anti-PD-1, IV Anti-PD-1, IA ethyl alcohol+IA Anti-PD-1, IA ethyl alcohol+IV Anti-PD-1, and IV ethyl alcohol+IV Anti-PD-1, are taken. The results show that IA ethyl alcohol can mediate checkpoint inhibitor anti-PD-1 antibody brain tumor entry.

Experiment 8

Immunohistochemistry staining was performed to detect the spreading of CD8-positive cells inside the experimental mouse brains bearing syngeneic mouse glioma from untreated control mice, conventional IV anti-PD-1 treated mice, and IA ethyl alcohol with Anti-PD-1 antibody-treated mice.

Figure 7:
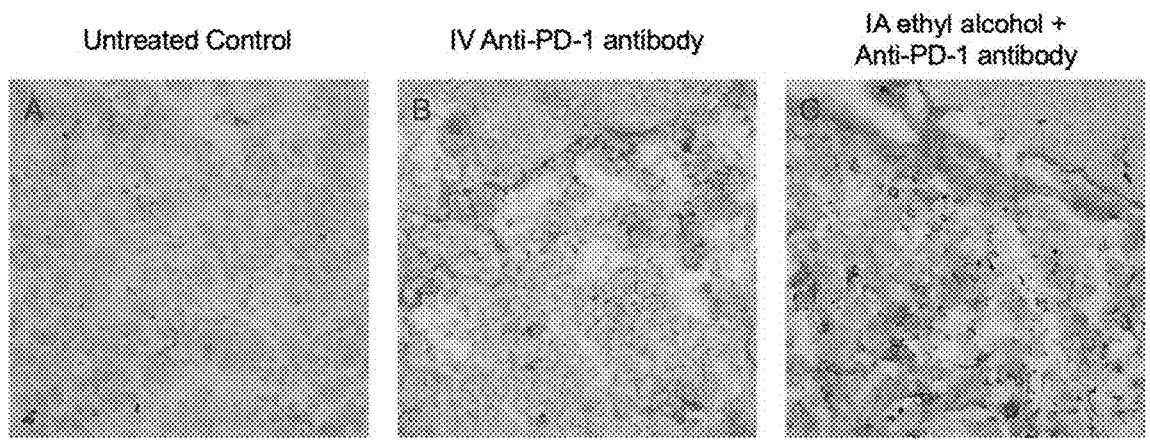
FIG. 7 illustrates the immunohistochemistry staining results of the replenished CD8+ cells in the intracranial mouse glioma tissues, including the following three animal groups, 1) the untreated control; 2) IV Anti-PD-1 antibody; and 3) IA ethyl alcohol+Anti-PD-1 antibody.

Standard protocols for immunohistochemistry are followed. The primary antibody is rabbit anti-CD8 (ab4055, Abcam). Three independent experimental fields are examined, and images are analyzed and quantitated using ImageJ software of the National Institutes of Health. The results of untreated control, IV Anti-PD-1 antibody, and IA ethyl alcohol+Anti-PD-1 antibody are shown in FIG. 7 of the drawings.

The comparison of the replenished CD8+ T lymphocytes induced inside the tumor of the three groups: untreated control, IV Anti-PD-1 antibody, and IA ethyl alcohol+Anti-PD-1 antibody shows that IA ethyl alcohol+Anti-PD-1 antibody can significantly enhance the replenishment of CD8+ T lymphocytes induced inside the tumor.

Experiment 9: Western Blot Experiment

Western blot analysis is performed to quantify the tight junction protein expression from the mice treated with and without IA ethyl alcohol. The membrane and cytosolic proteins are extracted with a MEM-PER™ Plus Membrane Protein Extraction Kit (ThermoFisher Scientific, Waltham, MA USA). Proteins are separated by SDS-PAGE and transferred to nitrocellulose membranes. Primary antibodies used are rabbit anti-claudin-3 (ab15102), rabbit anti-claudin-5 (ab15106), rabbit anti-claudin-6 (ab99226), rabbit anti-JAM (ab125886), rabbit anti-occludin (ab222691, 1:200, Abcam, Cambridge, MA USA), and mouse anti-β-actin (66009, 1:1000, Proteintech, Rosemont, IL USA). Secondary antibodies used are HRP-conjugated goat anti-mouse (SA00001, 1:2500, Proteintech) and goat anti-rabbit (7074, 1:2500, Cell Signaling Technology).

Endothelial cells (ECs) form the inner lining of the vessel wall, and perivascular cells, referred to as pericytes, and vascular smooth muscle cells or mural cells, envelop the surface of the vascular tube. The BBB possesses specific characteristics (i.e., tight junction protein complexes, influx, and efflux transporters) that control the permeation of circulating solutes, including therapeutic agents. Due to the complexity and integrated structures, BBB controls the crossing of chemicals and prevents toxic material from the circulation entering the brain. Structurally, BBB is reliant on non-fenestrated EC that form the blood vessel wall and is supported by both pericytes and astrocytes. Pericytes can modulate and maintain the BBB through the release of signaling factors to determine the number of EC tight junctions as a physical barrier and direct the polarization of astrocyte end feet. A reduction in pericyte numbers can cause a loss of tight junctions between EC, leading to increased BBB permeability. Also, pericytes can control the movement of substances between the bloodstream and the brain parenchyma, including the vascular clearance of toxic species out of the brain. The tight junction is essential for establishing a barrier against free diffusion between different extracellular compartments as well. The tight junctions (TJs) are protein complexes that, through intercellular interactions, obliterate the paracellular space to form a paracellular diffusion barrier. Some of them have been identified as transmembrane proteins named as occludins. Claudins, are the main structural proteins of tight junction strands. They interact with the long C-terminal cytoplasmic tail of claudin and JAM (junctional adhesion molecule) in the membrane. Also, Pgp, an ATP-binding cassette (ABC) efflux transporter, is predominantly expressed on the luminal (blood-facing) surface of the BBB endothelium, where it serves as a functional barrier in regulating the passage of a wide variety of endo- and xenobiotic compounds out of the central nervous system. The disruption of the physical barrier of the BBB impedes the effective delivery of the drugs into the brain. The tight junction proteins that are supposed to maintain the integrity of BBB include occudins, claudin, and junction adhesion molecules, etc.

Figure 8:
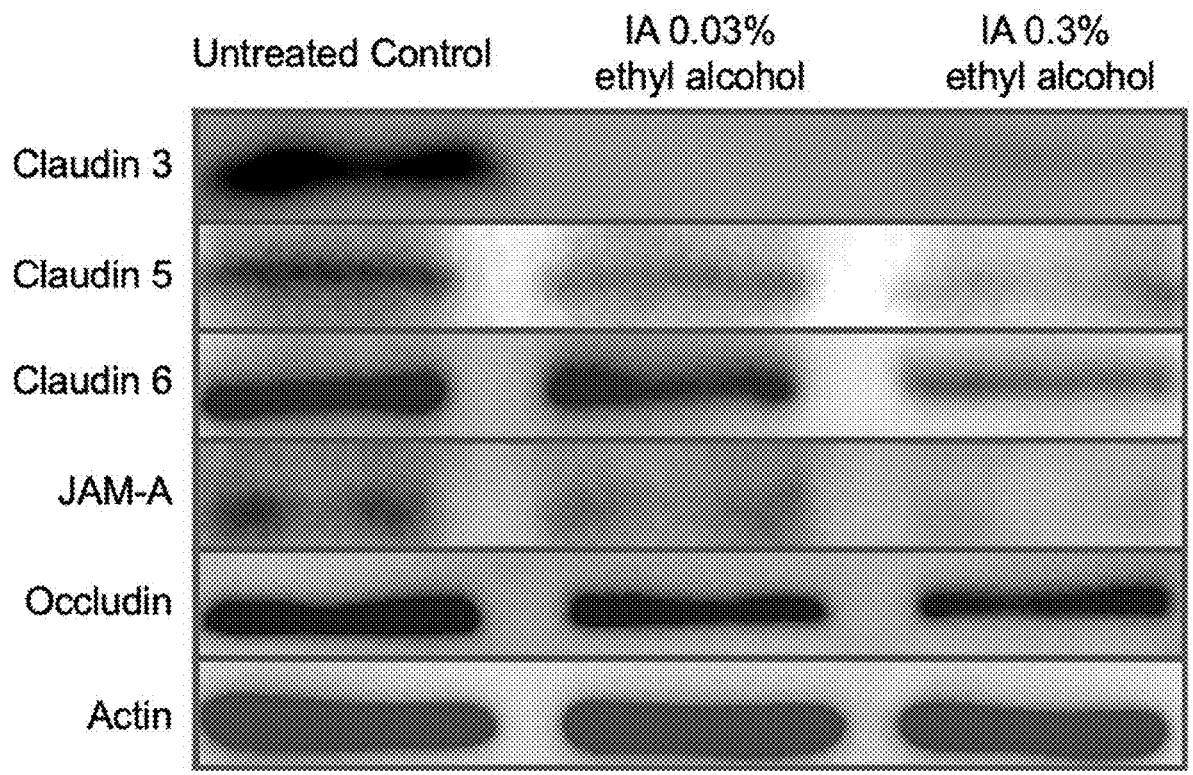
FIG. 8 illustrates the results of Western Blot analysis. The quantified tight junction proteins in the brain tissues were harvested from the experimental mice treated with and without IA ethyl alcohol.

Western Blot examined and quantified the tight junction proteins in brain tissues. The experimental mice treated with IA 0.03% ethyl alcohol, IA 0.3% ethyl alcohol, and a control group without IA ethyl alcohol treatment are examined. The results are shown in FIG. 8 of the drawings.

Experiment 10: Ultrasound-Guided Intracardiac (IC) Injection in Experimental Rats 1. Set up the ultrasound imaging system before anesthetizing the rats; to anesthetize the rats in an induction chamber using 3-4% isoflurane in 100% oxygen at a rate of 0.2-0.5 L/min; to confirm proper anesthetization before performing imaging by pinching the toe, rolling the rats.
2. Remove the fur over the thorax area using hair removal cream.
3. Place the experimental animal on the imaging table in the supine position and secure both the upper and lower limbs with adhesive tape to avoid body movement during the procedure.

4. Clean up the skin of the thorax area using a 10% povidone/iodine swab followed by a 70% ethanol swab. Apply a thick layer of gel to the thorax area of the animal.
5. Mount the transducer and adjust the position until the left ventricle is clearly visible.
6. Load 350 µl varied concentrations of Ethyl Alcohol (EA, from 0.01%-5%) in 2% EB solution into a 1-mL syringe with a 30 1G needle and secure the syringe to the appropriate holder. To visualize pulsating blood, keep a small air column in the syringe; advance the syringe towards the animal thorax, adjust the needle trajectory using the ultrasound guidance, and enter the left ventricle, and to complete the IC injection within 30 seconds.
7. Withdraw the needle, release that rat, and monitor until complete recovery from anesthesia The rats are treated with varying concentrations of EA via intracardiac injection. The ethyl alcohol concentrations are 3%, 1%, 0.3%, 0.1%, and 0.01%. Sham control (without treatment as negative control) is included in this experiment. Even blue is used as a non-BBB permeable substance to study the ethyl alcohol (via intracardiac injection) medicated BBB opening. After treatment, photographs are taken from superior and inferior views of the brains removed from the rats.
Results
The tinted blue color, which stands for the extravasated dye, Even's blue, is observed in all treatment groups. No color is observed for the sham control group. This indicates that the ethyl alcohol (via intracardiac injection) can medicate BBB opening for delivery of non-BBB permeable substance (Even's blue).

Experiment 11: Relationship Between the Injection Site and Distribution of BBB Opening The seven major branches of the internal carotid artery (ICA) are the meningohypophyseal artery, the ophthalmic artery, the posterior communicating artery, the middle cerebral artery, the anterior cerebral artery, and the anterior communicating artery. As the ophthalmic artery is the first major branch derived from the ICA, the extravasated EB from the disrupted BBB stained the eye (left) blue, a critical indicator of BBB opening.
Fisher 344 rats are used for placing left-side intraarterial (IA) catheters and injecting ethyl alcohol (EA)+2% EB. Photographs of the rats in the prone and supine positions are taken for observation and further analysis.
Results
The extravasated EB spreading inside the left vitreous humor, but not inside the right is observed in photographs of Fisher 344 rats in the prone/supine position.
The results indicate that the point of entry of ethyl alcohol can lead to a localized extravasated EB spreading.

Experiment 12: Comparison of the Hyperosmotic Agent, Mannitol and Ethyl Alcohol-Mediated BBB Disruption Hyperosmotic-induced BBB disruption is accomplished by intracarotid infusion of a hypertonic mannitol solution is mediated by vasodilatation and shrinkage of cerebrovascular endothelial cells, with the widening of the inter-endothelial tight junctions. The following conditions must be required to make it possible. 1). High concentration 25%; 2). Need to be prewarmed to 37° C. before the application; 3). High pressure to maintain a high-speed injection; and 4). Large injection volume. The following three groups are performed:
A. 1800 µl 25% mannitol infused in 30 seconds (the minimum volume at 0.06 ml/s, 30 seconds). B. 300 µl 3% USDA Organic EA infused in 5 seconds (in room temperature, and at the injection speed of 0.06 ml/s, 5 seconds). C. 300 µl 25% mannitol infused at regular speed in 1 minute (warmed up to 37° C. before the application).
Photographs of the animal in the prone position and the brain are taken for observation and further analysis.

Results

EB is observed in both groups A and B. EB is not observed in group C. Therefore, induced BBB disruption is achieved in both groups A and B, but not C.

Experiment 13A: Ethyl Alcohol Mediated BBB Disruption via an Intraarterial Catheter Placed in the Left Internal Carotid Artery Experimental rats are treated with varying concentrations of IA EA (in room temperature, 300 µl 5%, 3%, and 1% EA infused slowly in 1 minute, respectively) and are applied through the arterial catheter placed into the left internal carotid artery. The photographs of the rats in the prone position, the perfused rat brains (superior/inferior view), and the coronal sections of the rats are taken 2 hours after the IA injection of a mixture of EA+2% EB.
The coronal sections demonstrate the extravasated EB spreading out homogeneously through almost the whole section of the left hemisphere of the brain.

Experiment 13B: EA Mediated BBB Disruption Via Intraarterial Catheter Placed in Left Internal Carotid Artery Experimental rats are treated with varying concentrations of IA EA (in room temperature, 300 µl 0.3%, 0.1%, and 0.01% EA infused slowly in 1 minute, respectively). They are applied through the arterial catheter placed into the left internal carotid artery. The photographs of the rats in the prone position, the perfused rat brains (superior/inferior view), and the coronal sections of the rats are taken 2 hours after the IA injection of a mixture of EA+2% EB.
The lower concentrations of EA-induced BBB disruption can be differentiated from the perfused brain tissues (the superior/inferior view) and the dissected coronal section of the brain. Even at the lowest concentration of EA, 0.01% (at room temperature, infused slowly in 1 minute), the extravasated blue EB can still be visualized in the left hemisphere of the brain tissue.

Experiment 14: The Detection of Autofluorescence from EB Dye by Confocal Microscopy The rapid visualization of the extravasated EB/albumin conjugate distribution after IA catheter delivery of 3% EA by fluorescence from EB dye by confocal microscopy is performed.
The fluorescence from EB dye permits the rapid visualization of extravasated EB/albumin conjugate distribution after IA catheter delivery of 3% EA. An untreated rat group is used as a control. IA 3% EA+2% EB solution treatment is used as the testing group.
The photographs of cryostatic brain sections from an untreated rat are stained with DAPI to illustrate the background nuclear staining under confocal imaging, respectively. The photo-/micrographs and magnified confocal images of the brain from the rat treated with IA 3% EA+2% EB solution are obtained for studies and comparison. The micrograph of the whole brain section is scanned by confocal microscopy to obtain the confocal images. The confocal images are further enlarged for observation.

In the photo-/micro-graphs of the brain from the rat treated with IA 3% EA+2% EB solution, the majority of extravasated EB can be visualized (blue color in the photograph and pink color in the micrograph) in the left hemisphere of the brain section; the autofluorescence of EB/albumin can be detected. The micrograph of the whole brain section demonstrates that a massive spreading of autofluorescence (dark red color) from EB/albumin can be detected in the brain's left hemisphere. The micrograph with magnified confocal images show an extensive spreading EB in red (magnification 63×; the scale bar, 50 μm).

Experiment 15: Intraarterial EA-Mediated Antibody Delivery into Normal Rat Brain Ethyl alcohol mediated antibody brain entry via catheter placement through the internal carotid artery (left). The experimental rat is treated with IA 3% EA+50 μg goat anti-rat IgG (H+L) ALEXA FLUOR® 647 (ab150167, Cambridge, MA USA) via the left internal carotid artery catheter. The micrograph of the whole brain section is scanned with a fluorescence microscope. Two sections from the right and left hemispheres of the brain are selected respectively and are enlarged with a magnification of 63×. The scale bar used is 50 μm. The images of the left and right hemispheres, and the enlarged sections are studied.

Results

The left hemisphere has more dense fluorescence than the right hemisphere and more dispersed antibodies labeled with ALEXA FLUOR® 647.

The fluorescence represents the spreading of the dispersed antibodies labeled with ALEXA FLUOR® 647. In other words, ethyl alcohol can mediate an immediate and efficient BBB opening, and the concentration of the non-BBB substance can be controlled through the site of injection.

Experiment 16: The Comparison of Goat Anti-Rat IgG (H+L) ALEXA FLUOR® 647 in the Experimental Rats EA-mediated antibody (goat anti-rat IgG (H+L) ALEXA FLUOR® 647) brain entry via catheter placement through the internal carotid artery (left) are tested. The cryosection photographs and images from the confocal microscope after EA treatment are taken for studies. An EA-untreated group is used as a control group. IA antibody [50 μg goat anti-rat IgG (H+L) ALEXA FLUOR® 647] and IA 3% EA+antibody [50 μg goat anti-rat IgG (H+L) ALEXA FLUOR® 647 are the two comparison groups.

Results

The corresponding images from the confocal microscope (the blue DAPI is used to stain the nuclear as background staining; the testing antibody (goat anti-rat IgG (H+L) ALEXA FLUOR® 647) is stained with pink color, and the yellow color is used to for the merged images from DAPI and antibody) are obtained. An even and widely spread pink color is observed in the IA 3% EA+antibody [50 μg goat anti-rat IgG (H+L) ALEXA FLUOR® 647 group while some pink color is observed in the IA antibody [50 μg goat anti-rat IgG (H+L) ALEXA FLUOR® 647] group. The results indicate that IA 3% EA can mediate the entry of the antibody effectively.

Experiment 17: The Comparison of ALEXA FLUOR® 647 Anti-Human IgG in the Experimental Rats An ALEXA FLUOR® 647 anti-human IgG antibody was applied via IA catheter delivery to rule out the nonspecific binding to the experimental rats. 3% EA-mediated antibody brain entry via catheter placement through the internal carotid artery (left) is tested and compared. The cryosection photographs and images from the confocal microscope after EA treatment are taken for studies. An EA-untreated group is used as a control group. IA antibody [50 μg ALEXA FLUOR® 647 anti-human IgG antibody (ab201841); and IA 3% EA+50 μg ALEXA FLUOR® 647 anti-human IgG antibody (ab201841, Cambridge, MA USA) are the two comparison groups.

Results

The corresponding images from the confocal microscope (the blue DAPI is used to stain the nuclear as background staining; the testing antibody (ALEXA FLUOR® 647 anti-human IgG antibody) is stained with pink color, and the yellow color is used for the merged images from DAPI and antibody).

The EA+antibody group illustrates an even and widely spread pink color, while the antibody-only group has some pink color. The results indicate that IA 3% EA can effectively mediate the antibody's brain entry.

Experiment 18: Pharmacodynamic Study

To validate the intervals of the opened window of the breached BBB. A detailed pharmacodynamic study was performed to evaluate the potential of intracardiac EA-mediated transient BBB openings to deliver the non-BBB permeable EB dye into the brain.

The experimental mice are treated with an ultrasound-guided intracardiac injection of the optimal concentration of EA (0.3%, v/v), followed by the intravenous infusion of 2% EB dye via the tail vein catheter at different time points (with an interval of every 15 minutes).

Figure 9:
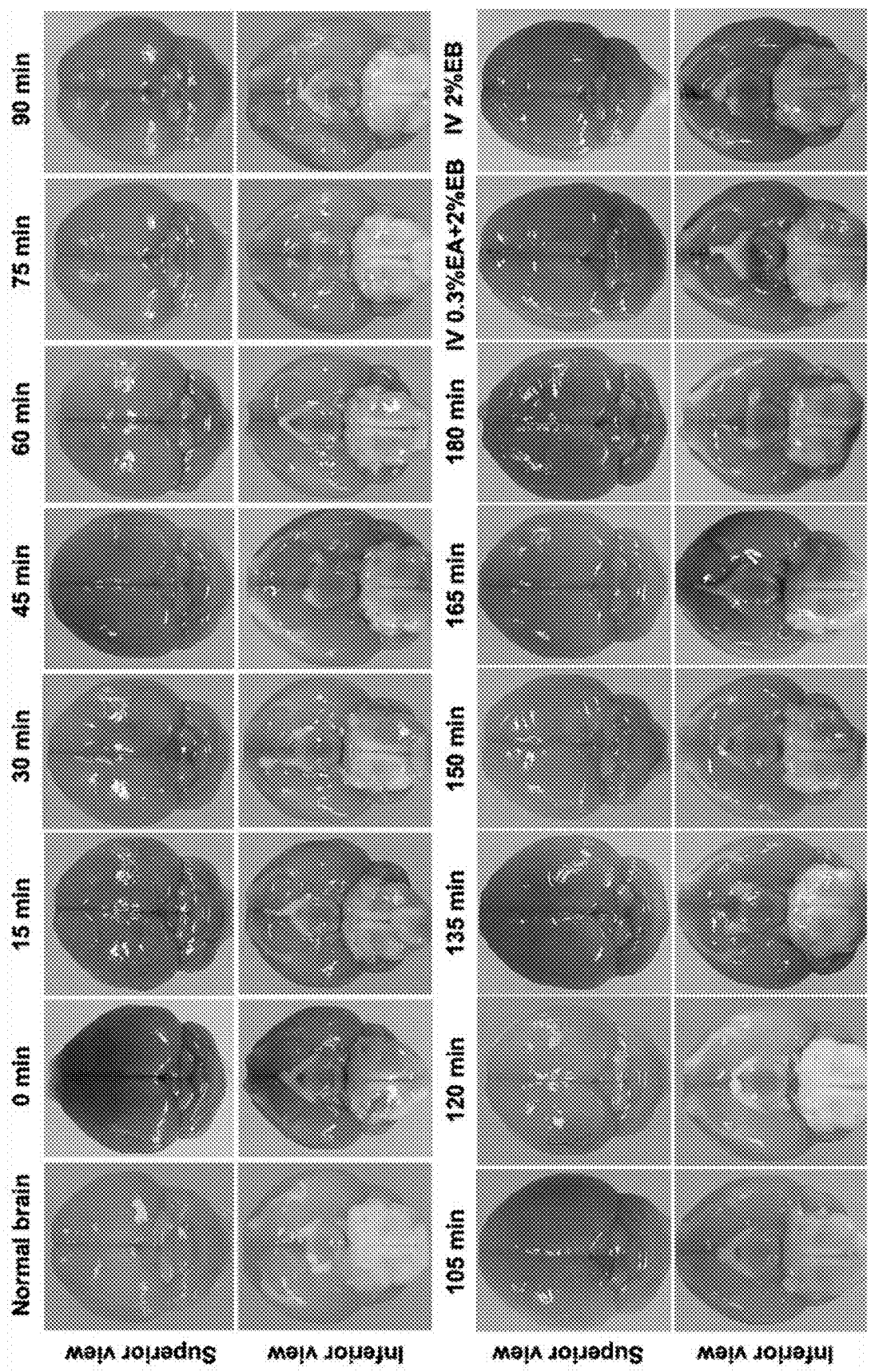
FIG. 9 illustrates the results of the detailed pharmacodynamic study for IA 0.3% ethyl alcohol-mediated BBB opening in Experiment 18.

EB dye is used as a non-BBB-permeable substance. Any extravasated blue color observed in the brain tissues indicates that the BBB is disrupted and leaky. The non-BBB-permeable substance could be penetrated and spread out to the brain tissues. Photographs of the perfused brain tissues harvested at different time points are taken for observation and comparison, as shown in FIG. 9 of the drawings.

Results

The listed perfused brain tissue photographs show varied densities of blue color spread during the BBB restoration process at different times post-IA 0.3% EA injection. For example, at "0 min," the experimental mouse is euthanized immediately after the IA 0.3% EA and intravenous infusion of 2% EB dye via the tail vein catheter. This extravasated EB dye at this "0 min" time point demonstrates that IA EA can lead to an immediate, homogeneous, and highly efficient BBB opening.

The gradient of the leaked EB dye color from dark blue to very faint blue takes about two hours (120 minutes), and no blue is observed after that. Accordingly, this pharmacodynamic study provides solid evidence that the intracardiac EA-mediated transient BBB opening lasted up to two hours (120 minutes).

This pharmacodynamic study demonstrated that IA EA could 1) induce an immediate BBB opening, 2) lead to a homogenized spread of the non-BBB permeable EB dye, 3) restore the disrupted BBB to an intact status for up to 120 minutes (a transient 2-hour BBB opening window). 4) lead to a safe manipulation (occasional adverse effects, such as mild epilepsy, but no moderate to severe epilepsy and sudden death were observed).

As a negative control, photographs of perfused brain tissues were taken from the following animals: the normal untreated mice; the mice were intravenously administered 2% EB; and the mice received the same dose of 0.3% EA mixed with a 2% EB solution intravenously as applied via intracardiac injection. No extravasated EB dye in any parts of the brain without IA EA-induced BBB opening.

Comparative Experiment 19

The major difference between IA EA- and IA NEO100-mediated BBB opening in the experimental animals is compared.

Due to multiple differences between EA and NEO100 in chemical structure, polarity, hydrophilic, lipophilic, etc., the BBB opening initiated by the IA EA and IA NEO100 are compared in this study.

Intracardiac injected various concentrations of EA (at 25%, 20%, 3%, 0.3%, and 0.1%, 0.03%, 0.01%) and NEO100 (at 25%, 20%, 3%, 0.3%, and 0.1%, 0.03%, 0.01%) are used on mice to test their effects on BBB disruption and evaluated by the observation of extravasated EB dye in the brain tissues. Extravasated EB dye is used as the non-BBB permeable substance. Any blue color observed in the brain indicates that the breached BBB and the EB dye are delivered to the brain. Photographs of the perfused brain tissues from the experimental mice treated with intraarterial EA and NEO100 are taken for observation and comparison.

Results

Figure 10A:
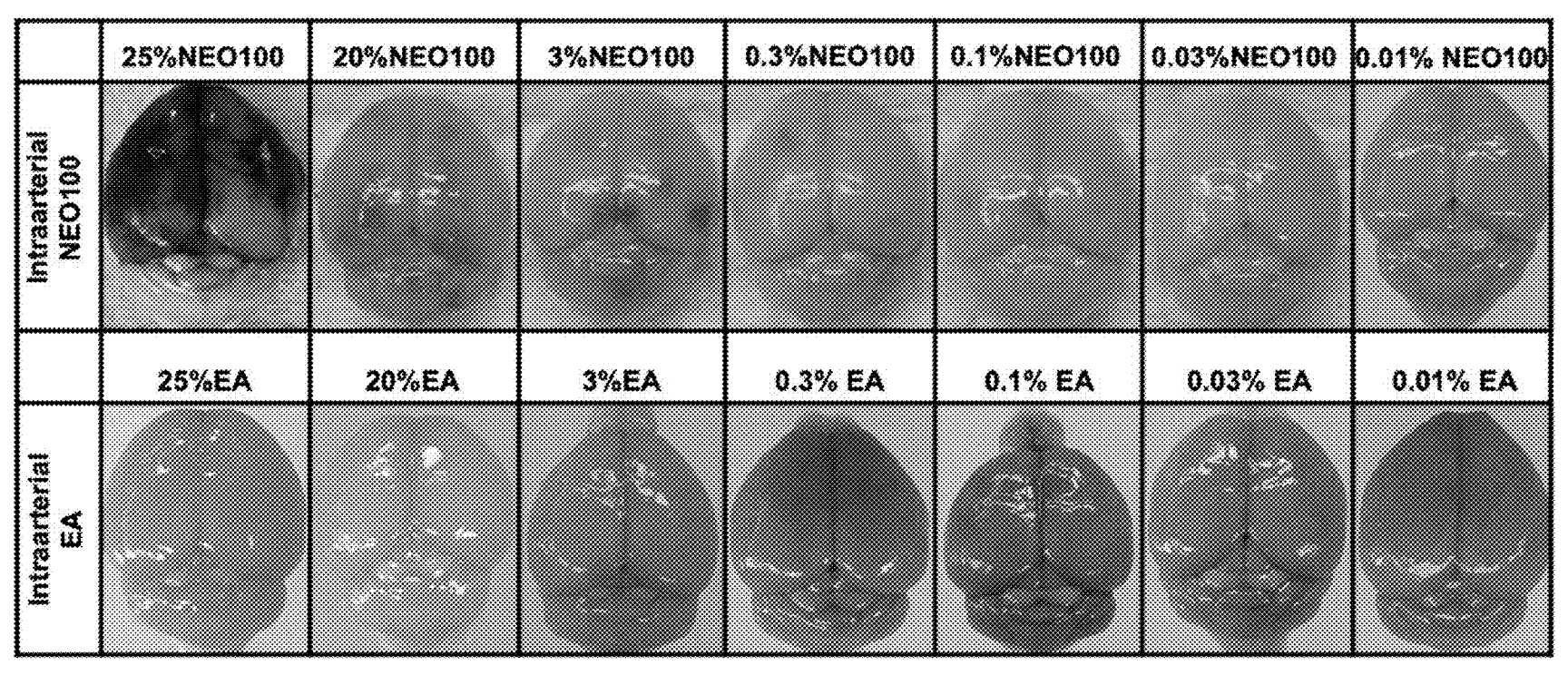

As shown in FIG. 10A, intraarterial NEO100-mediated BBB disruption occurs in a dose-dependent manner. The higher the concentration, the stronger the breached BBB induced. On the contrary, the intraarterial EA-mediated BBB opening exhibits a dose-reverse response. This means the higher the dose of EA, the lesser the effect on the BBB opening. This unique property is a "plus" that contributes to safety considerations and prevents the unnecessary adverse impacts that high doses of EA may cause.

Due to NEO100's intermediate polarity, lipophilicity, and water-insolubility, the suspended floating particles (100% NEO100) result in a unique BBB opening in a random, haphazard, non-homogenized, patchy, or punctate pattern.

IA 0.1% EA-mediated BBB opening illustrates an entirely different mode. The spread of non-BBB permeable EB dye is even and homogeneous. This specificity will confer a crucial clinical advantage over the random, patchy, or punctate patterns induced by IA NEO100. More importantly, the EA solution can be accurately controlled by applying the serial dilution technique, regardless of the desired concentration.

Figure 10B:
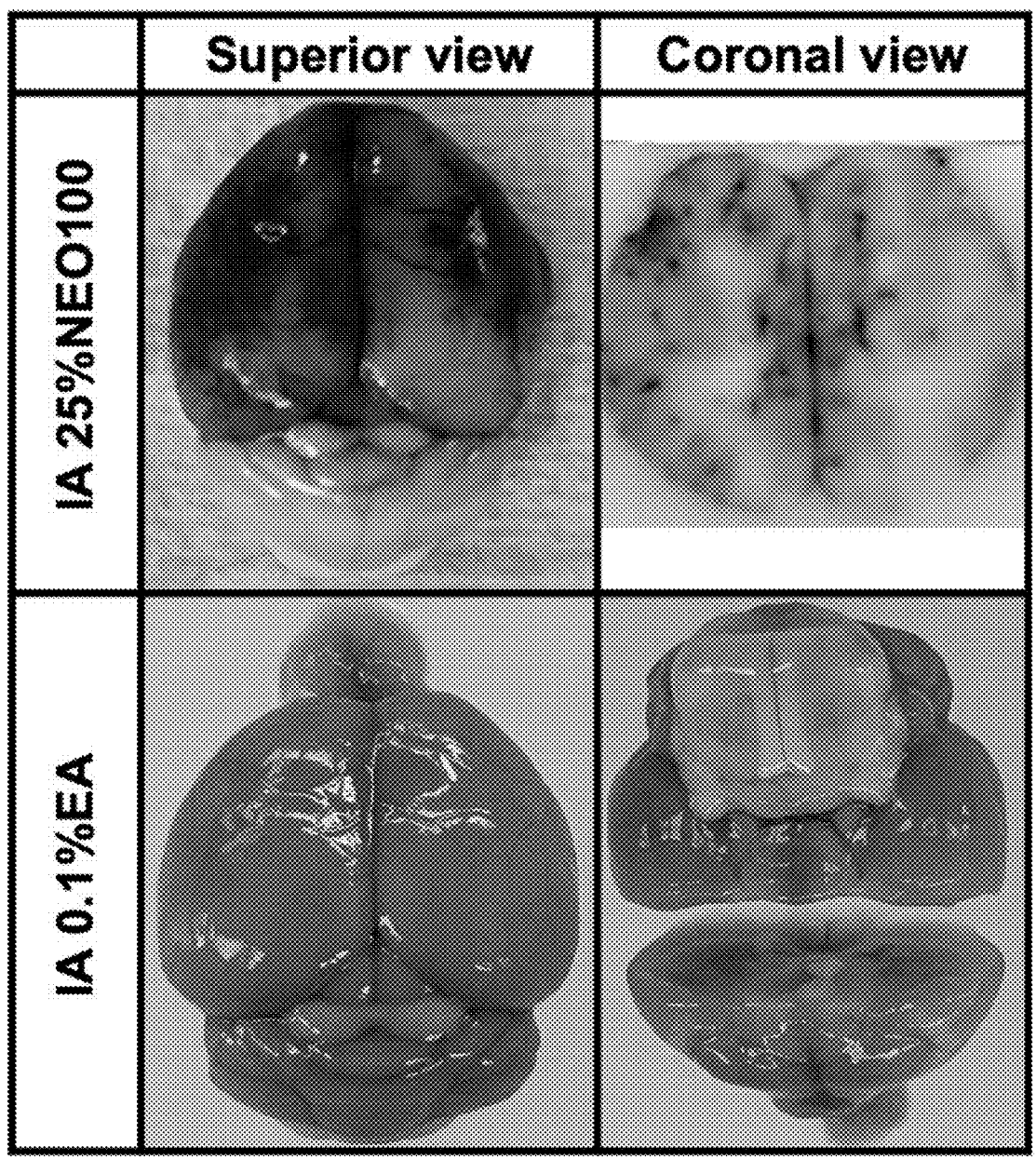

FIG. 10B shows photographs of the coronal section from the mice treated with IA 25% NEO and IA 0.1% EA. The data further support the findings that the NEO100 breached BBB is in a random, haphazard, sporadic, patchy, or punctate pattern, leading to an uncontrollable penetration of non-BBB permeable EB dye. Compared to the IA EA, which induced a homogenized BBB opening and led to an evenly spread of the non-BBB permeable EB dye inside the brain.

Experiment 20

The same procedure as experiment 19 was performed with IA 0.3% NEO100 with 2% EB dye solution.

Figure 11:
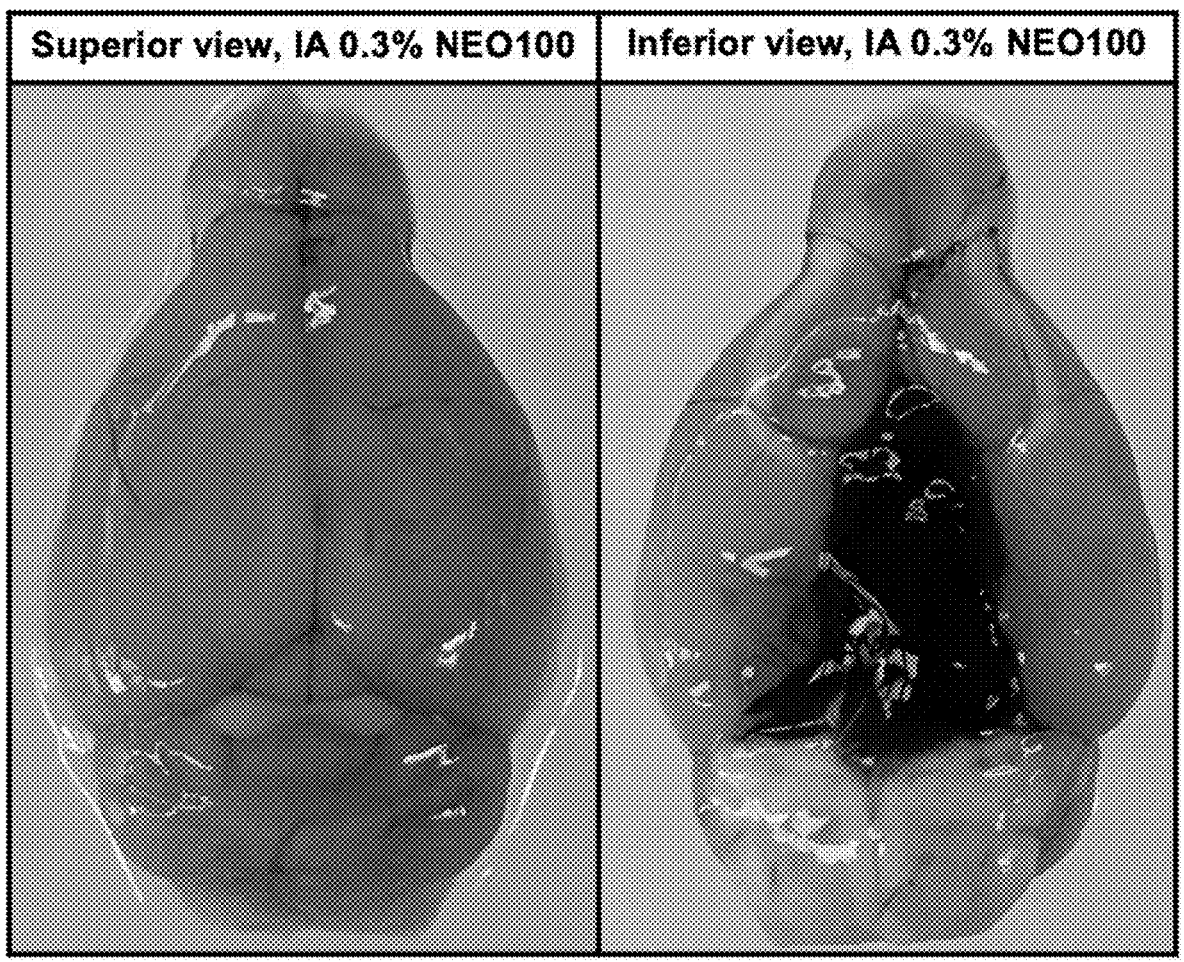
FIG. 11 illustrates the harvested brain tissue from the sudden death mouse treated with IA 0.3% NEO100.

As illustrated in FIG. 11 of the drawings, the photographs of the superior/inferior view of the perfused mouse brain tissue harvested from a sudden-death mouse right after the treatment.

The inferior-view photograph of the brain shows bleeding and a blood clot. We speculate that the bleeding came from the damaged cerebral vasculature along the circle of Willis. This severe adverse effect may be caused by the large, pure NEO100 particle attached to the vasculature wall and damaged the vessel. As mentioned earlier, the lipophilic, water-insoluble NEO100 can't be diluted in an aqueous solution as low as stated, such as 10%, 3%, 0.3%, or even lower concentrations. The actual effect is from the suspended particle containing 100% NEO100, not the indicated 0.3% NEO100.

Therefore, the stated concentrations of NEO100 in water are problematic and misleading. In other words, the indicated concentration of NEO100 is inaccurate. Due to the lipophilic nature, a significant caveat exists without an appropriate solvent to dilute this lipophilic NEO100 to a desired concentration.

Experiment 21: Comparison of the Toxicity of IA NEO100 and IA EA

The safety profile of IA 0.3% NEO100 vs. IA 0.3% EA are compared. Table 4 demonstrates the possible adverse effects of the experimental mice treated with IA NEO100 and IA EA. There are 15 experimental mice in each testing group. The potential adverse effects are evaluated. 1) frequency of immediate sudden death (right after the intracardiac injection); 2) long-term epilepsy lasting ≥6-12 hours post-injection and leading to death; 3) intermediate epilepsy lasting 2-6 hours post-injection and leading to death; 4) intermediate epilepsy lasting 2-6 hours post-injection before survival to fully recovery; 5) transient or occasional epilepsy lasting shorter than ≤2 hours post-injection.

The results are shown in Table 4 as follows:

| Possible Adverse Effect | IA Injection 0.3% NEO100 | IA Injection 0.3% EA |
|---|---|---|
| Immediate Sudden Death | 3 | 0 |
| Long-lasting epilepsy post-injection leading death | 3 | 0 |
| Intermediate-lasting epilepsy post-injection leading to death | 2 | 0 |
| Moderate-lasting epilepsy post-injection and survival to fully recovery | 3 | 3 |

-continued

| Possible Adverse Effect | IA Injection 0.3% NEO100 | IA Injection 0.3% EA |
|---|---|---|
| Transient, mild, or occasional epilepsy post-injection and survival to fully recovery | 4 | 3 |
| Mortality | 53.33% | 0% |

In this study, the mortality of 0.3% NEO100 is 53.33%, while the mortality of EA is 0%. Also, in the IA NEO group, almost all of the tested animals experienced some degree of adverse effect, ranging from transient or occasional epilepsy to death. On the contrary, less than 50% of the tested animals in the EA group experienced adverse effects. These adverse effects are mild, ranging from transient or occasional epilepsy to moderate-lasting epilepsy before survival to full recovery, and no animal is found dead. In other words, using IA EA for BBB opening has generated much safer results than IA NEO100, which is an unexpected result.

Repeated comparative experiments of IA EA and IA NEO100 have been carried out. The results show that the overall mortality rate for IA NEO100 is around 60%, compared to a significantly lower mortality rate in IA EA-treated animals, which is less than or equal to 1% or sporadically.

It is worth mentioning that the IA EA has a shorter interval window of about 2 hours (120 minutes) of the breached BBB. This shorter, brief interval window confers great advantages and produces significant impacts compared to the longer ones, such as 4 hours for IA NEO100 and 6-7 hours for IA mannitol. This unique property contributes to safety considerations and prevents the unnecessary adverse impacts it may cause. Also the EA can result in an even, homogeneous spread of non-BBB substances into the brain parenchyma, which is another crucial indicator of the safety issue closely correlated with the breached integrity of the BBB.

One skilled in the art will understand that the embodiment of the present invention, as shown in the drawings and described above, is exemplary only and not intended to be limiting.

It will thus be seen that the objects of the present invention have been fully and effectively accomplished. Its embodiments have been shown and described to illustrate the present invention's functional and structural principles and are subject to change without departing from them. Therefore, this invention includes all modifications encompassed within the spirit and scope of the following claims.

What is claimed is:

1. A method of inducing an immediate and transient, blood-brain barrier (BBB) opening for delivery of a non-BBB permeable substance to a brain of a subject, comprising the steps of:
   (a) preparing an ethyl alcohol (EA) having a concentration by serial dilution with purified water or 0.9% NaCl; and
   (b) administering via injection said ethyl alcohol (EA) as a sole active ingredient into an arterial bloodstream of the subject to immediately induce a homogeneous distribution of said non-BBB permeable substance inside the brain of the subject,
   wherein said ethyl alcohol (EA) has a concentration of 0.01%-5% v/v at an injection site, and said ethyl alcohol (EA) reaches the brain of the subject to induce a transient opening of the blood-brain barrier for an opening time frame of not more than 2 hours so that the non-BBB permeable substance is capable of penetrating the blood-brain barrier to reach the brain of the subject during said opening time frame.

2. The method, as recited in claim 1, wherein said non-BBB permeable substance comprises a therapeutic agent, a diagnostic agent, or a prophylactic agent, and said non-BBB permeable substance is administered to the subject before, at the same time, or not more than 120 minutes after the ethyl alcohol (EA) is administered intraarterially to the subject.

3. The method, as recited in claim 1, wherein said ethyl alcohol (EA) reduces the level of tight junction proteins in at least a portion of the blood-brain barrier for a time frame of not more than 120 minutes immediately after the ethyl alcohol is administered to the subject, then the blood-brain barrier is restored to normal, blocking the non-BBB permeable substance from entering the brain.

4. The method, as recited in claim 2, wherein said ethyl alcohol (EA) reduces the level of tight junction proteins in at least a portion of the blood-brain barrier for a time frame of not more than 120 minutes immediately after the ethyl alcohol is administered to the subject, then the blood-brain barrier is restored to normal, blocking the non-BBB permeable substance from entering the brain.

5. The method, as recited in claim 1, wherein said ethyl alcohol (EA) has a concentration of 0.1%-0.3% v/v, and the purified water and the 0.9% NaCl meets USP standards.

6. The method, as recited in claim 1, wherein said ethyl alcohol (EA) is administered by ultrasound-guided intracardiac injection through a left-side intraarterial catheter placement for producing a localized left-side delivery of the non-BBB permeable substance.

7. The method, as recited in claim 1, wherein said ethyl alcohol (EA) is administered via ultrasound-guided intraarterial injection or intracardiac injection, an infusion flow rate is about 5-7 µl/second (0.3-0.45 ml/min), and an infusion volume is about 10% of a body weight (at 1 µl/g, volume/weight ratio) of the subject.

8. The method, as recited in claim 4, wherein said non-BBB permeable substance is one or more selected from the group consisting of: a small molecular tracer, EB (Evans Blue) dye, a cancer therapeutic agent, doxorubicin, an antibody, an antibody fragment, Trastuzumab, a checkpoint inhibitor, an anti-PD1 antibody or a PD1-binding fragment thereof, a monoclonal antibody, a peptide, a growth factor, a cytokine, and an enzyme.

9. The method, as recited in claim 1, wherein said non-BBB permeable substance is Trastuzumab or an anti-PD-1 antibody.

10. The method, as recited in claim 4, wherein said non-BBB permeable substance is Trastuzumab or an anti-PD-1 antibody.

11. A method for delivery of a therapeutic agent, a diagnostic agent, or a prophylactic agent into a brain of a subject, comprising the steps of:
    (a') adjusting a concentration of ethyl alcohol (EA) by using purified water or 0.9% NaCl;
    (b') administering said ethyl alcohol via injection as a sole active ingredient for opening a blood-brain barrier (BBB) of the brain of the subject into an arterial bloodstream of the subject, wherein a concentration of said ethyl alcohol is 0.01%-5% v/v, and
    (c') administering an effective amount of the therapeutic agent, the diagnostic agent, or the prophylactic agent before, concurrently, or not more than 120 minutes after said ethyl alcohol is administered to immediately induce a homogeneous distribution of said therapeutic agent, said diagnostic agent or said prophylactic agent inside the brain of the subject, wherein said ethyl alcohol (EA) reaches the brain of the subject to induce a transient opening of the blood-brain barrier so that the therapeutic agent, the diagnostic agent, or the prophylactic agent penetrates the blood-brain barrier to reach the brain of the subject, then the blood-brain barrier recovers and is restored to normal status after 120 minutes, blocking non-BBB permeable substances from entering the brain.

12. The method, as recited in claim 11, wherein said ethyl alcohol (EA) reduces a level of tight junction proteins in at least a portion of the blood-brain barrier for a time frame of not more than 120 minutes immediately after the ethyl alcohol is administered to the subject.

13. The method, as recited in claim 12, wherein a concentration of said ethyl alcohol is adjusted by using purified water or 0.9% NaCl which meets USP standards.

14. The method, as recited in claim 13, wherein said therapeutic agent, said diagnostic agent, or said prophylactic agent is selected from the group consisting of Trastuzumab and an anti-PD-1 antibody.

15. The method, as recited in claim 11, wherein said ethyl alcohol (EA) reduces a level of tight junction proteins in at least a portion of the blood-brain barrier for a time frame of not more than 120 minutes immediately after the ethyl alcohol is administered to the subject, and said therapeutic agent, said diagnostic agent, or said prophylactic agent is selected from the group consisting of Trastuzumab and an anti-PD-1 antibody.

* * * * *